(12) United States Patent
Sailynoja

(10) Patent No.: US 11,554,082 B2
(45) Date of Patent: Jan. 17, 2023

(54) NANOCRYSTALLINE CELLULOSE CONTAINING DENTAL MATERIAL

(71) Applicant: Stick Tech Oy, Turku (FI)

(72) Inventor: Eija Sailynoja, Littoinen (FI)

(73) Assignee: STICK TECH OY, Turku (FI)

( * ) Notice: Subject to any disclaimer, the term of this patent is extended or adjusted under 35 U.S.C. 154(b) by 387 days.

(21) Appl. No.: 16/640,383

(22) PCT Filed: Aug. 13, 2018

(86) PCT No.: PCT/FI2018/050583
§ 371 (c)(1),
(2) Date: Feb. 20, 2020

(87) PCT Pub. No.: WO2019/058019
PCT Pub. Date: Mar. 28, 2019

(65) Prior Publication Data
US 2020/0352831 A1    Nov. 12, 2020

(30) Foreign Application Priority Data

Sep. 17, 2017 (FI) .................................... 20175829

(51) Int. Cl.
*A61K 6/898* (2020.01)
*A61K 6/30* (2020.01)
*A61K 6/887* (2020.01)

(52) U.S. Cl.
CPC .............. *A61K 6/898* (2020.01); *A61K 6/30* (2020.01); *A61K 6/887* (2020.01)

(58) Field of Classification Search
CPC combination set(s) only.
See application file for complete search history.

(56) References Cited

U.S. PATENT DOCUMENTS

| 6,116,901 A | 9/2000 | Kangasniemi |
| 6,197,410 B1 | 3/2001 | Vallittu et al. |
| 6,595,776 B2 | 7/2003 | Kangasniemi et al. |
| 6,733,288 B2 | 5/2004 | Vallittu et al. |
| 6,881,062 B2 | 4/2005 | Kangasniemi et al. |
| 6,979,702 B1 | 12/2005 | Ma et al. |
| 7,001,181 B2 | 2/2006 | Kangasniemi et al. |
| 7,235,290 B2 | 6/2007 | Vallittu et al. |

(Continued)

FOREIGN PATENT DOCUMENTS

| CN | 102884128 A | 1/2013 |
| CN | 103284889 A | 9/2013 |

(Continued)

OTHER PUBLICATIONS

Hong Dong et al., "Cellulose Nanocrystals as a Reinforcing Material for Electrospun Poly(methyl methacrylate) Fibers: Formation, Properties and Nanomechanical Characterization," 87 Carbohydrate Polymers 2488 (2012).

(Continued)

*Primary Examiner* — Peter A Salamon
(74) *Attorney, Agent, or Firm* — Timothy H. Van Dyke; Wolter Van Dyke Davis, PLLC

(57) ABSTRACT

The present invention relates to a dental material comprising a thermoset methacrylate-based polymer resin and cellulose nanocrystals, wherein the cellulose nanocrystals have been modified to be hydrophobic.

11 Claims, 3 Drawing Sheets

(56) References Cited

U.S. PATENT DOCUMENTS

| | | | |
|---|---|---|---|
| 7,435,764 B2 | 10/2008 | Vallittu et al. | |
| 8,735,470 B2 * | 5/2014 | Takizawa | C08J 3/226 536/56 |
| 2004/0106085 A1 | 6/2004 | Vallittu et al. | |
| 2006/0275734 A1 | 12/2006 | Vallittu et al. | |
| 2009/0258965 A1 | 10/2009 | Lassila et al. | |
| 2011/0201755 A1 * | 8/2011 | Hamad | C08L 1/286 525/63 |
| 2013/0289170 A1 * | 10/2013 | Takizawa | C08L 1/00 536/56 |
| 2016/0002462 A1 * | 1/2016 | Zhang | C09J 197/005 524/733 |
| 2017/0027168 A1 * | 2/2017 | Heath | A61P 17/00 |
| 2017/0283669 A1 * | 10/2017 | Lipscomb | C08F 220/1804 |

FOREIGN PATENT DOCUMENTS

| | | |
|---|---|---|
| CN | 103284889 B | 2/2015 |
| CN | 107669491 A | 2/2018 |
| EP | 0 872 218 A2 | 10/1998 |
| JP | 2004517107 A | 6/2004 |
| JP | 2007501276 A | 1/2007 |
| JP | 2015067543 A | 4/2015 |
| JP | 2016501937 A | 1/2016 |
| WO | 2002053107 A1 | 7/2002 |
| WO | 20040100900 A1 | 11/2004 |
| WO | 2008000917 A1 | 1/2008 |
| WO | 2011100818 A1 | 8/2011 |
| WO | 2014085729 A1 | 6/2014 |
| WO | 2014087053 A1 | 6/2014 |
| WO | 2014124541 A1 | 8/2014 |

OTHER PUBLICATIONS

Kargarzadeh et al., "Recent Developments on Nanocellulose Reinforced Polymer Nanocomposites: A Review," 132 Polymer 368 (2017).

European Patent Office Communication in Appln No. 18 762 899.5 dated Apr. 12, 2021.

CN Office Action, The State Intellectual Property Office of the People's Republic of China, dated Jan. 1, 2014, 10 pages.

Lin, Ning, "Cellulose nanocrystals: surface modification and advanced materials", Chemical and Process Engineering, 2014, English, 25 pages.

* cited by examiner

NANOCRYSTALLINE CELLULOSE CONTAINING DENTAL MATERIAL

FIELD OF THE INVENTION

The present invention relates to dental materials comprising methacrylate-based polymers.

BACKGROUND

The main function of a dental adhesive is to attach a dental filling composite on the surface of dentin, whenever a tooth has to be filled after the removal of a dental caries. However, known dental adhesives, which are generally methacrylate-based, have some problems with long-term durable attachment to the structure of dentin due to the hydrophilic nature of the dentin. As a result, adhesives may lack elasticity, and dental fillings may crack in their entirety. There exists thus a need to provide a dental adhesive that has better long-term properties than previously known adhesives.

Dentin is the major part of a tooth, located under the layer of protective enamel. In the root of the tooth, it is supported by cementum, which attach on the socket with a membrane known as periodontal ligament. Moreover, dentin encloses a space known as pulp cavity, which is filled by pulp. Dentin is generally a vital tissue, and similar to enamel, formed of minerals which concentration is however less compared to the tissue of enamel. Measured by weight, the composition of dentin is 68% minerals, 21% organic materials and 11% of water. The minerals are hydroxyapatite crystals, whereas the organic content of the dentin is 90% collagen and 10% non-collagen, including inter alia proteins, lipids, growth factors and enzymes.

Indeed, dentin has a complex structure, and the composition can be specified into different types of dentins. The peripheral outer layers of dentin are less mineralized than circumpulpal dentins, which form the majority of the dentin. Circumpulpal dentin forms the bulk of dentin, and it contains odontoblasts, the constant creators of new dentin. However, the circumpulpal dentin layer is not homogeneous, and it can further be characterised to be composed of intertubular dentin and peritubular dentin. Intertubular dentin is an essential part of the circumpulpan dentin, since its extracellular organic matrix is composed mostly of fibrous protein collagen type I.

Cellulose is a biopolymer, which can be found from several different sources, varying from plants to bacteria and algae. Due to the sustainable origin, as well as the high strength and stiffness coupled with relatively low density, cellulose has been widely examined during the past decades. Especially nanocelluloses, which can be further divided to nanofibrillar celluloses (NFCs) and cellulose nanocrystals (CNCs), have shown potential to be used as a reinforcement material and modification platform in different biomedical applications. Generally, nanometre scale, isolated cellulose structures are defined as nanocelluloses. Several designations for CNCs can be found in the literature, including whiskers, nanocrystals, nanoparticles, nanofibers, microcrystallites and microcrystals.

Document US 2011/201755 discloses thermoplastic nanocomposite material based on nanocrystalline cellulose. The document does not provide any thermoset polymers to be combined with the nanocrystalline cellulose.

An aim of the present invention is thus to provide a dental material that at least partially overcomes the problems of prior art. Indeed, it is an object to provide a dental material that has both hydrophilic and hydrophobic properties and is thus capable of attachment to the structure of dentin and to conventional dental filling materials.

DETAILED DESCRIPTION

Figure 1:
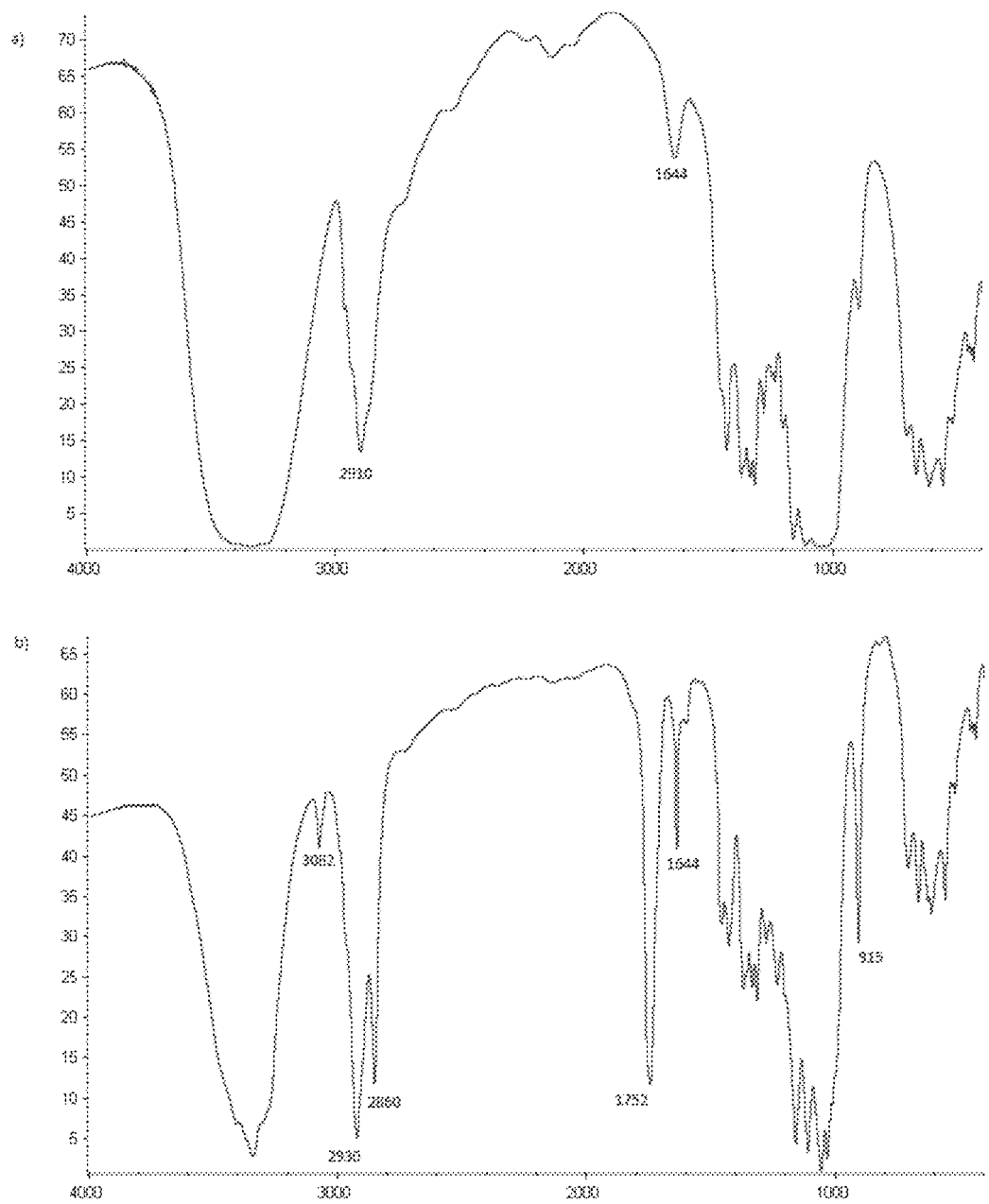
FIG. 1 illustrates FTIR spectra for pristine CNCs and modified CNCs.

The present description relates to a dental material comprising a thermoset methacrylate-based polymer resin and cellulose nanocrystals, wherein the cellulose nanocrystals have been modified to be hydrophobic.

The present description thus provides a dental material that at least partially solves the problem encountered in prior art, by providing a reinforcement of the dental material with a reinforcing material that has both hydrophilic and hydrophobic properties. Therefore, the material is able to attach to both the structure of dentin and to the dental filling material, and to improve the current dental materials by improving adhesion at the dentine-filling material interface. Furthermore, the CNC increases the viscosity of the dental material, thus making it easier and more reliable to use, as it will remain where it has been applied to, at least for as long as is required before it is polymerised and/or the dental filling material is applied. Furthermore, without wishing to be bound to a theory, it is suspected that the CNCs in the present dental material would be able to orientate, i.e. that their hydrophilic part would orientate towards the hydrophilic parts of the dentin, and the hydrophobic part of the CNCs would orientate towards the hydrophobicity of the dental filling material (typically the matrix of the dental filling material).

By thermoset, or thermosetting plastic, it is meat a plastic that is irreversibly cured from a soft solid or viscous liquid, prepolymer or resin. The process of curing changes the resin into an infusible, insoluble polymer network. Curing (polymerisation) may be induced by the action of heat or suitable radiation often under high pressure, or by mixing with a catalyst.

The present dental material comprises a polymer resin, i.e. a mixture of monomers that can be polymerised (cured) to form a polymer. The modified cellulose nanocrystals improve the strength of the material as well as improve the compatibility of the methacrylate resin with the dentin. The pH of the methacrylate resin can be acid, basic or neutral. In case the pH is too acid, the bonding strength is weaker and hydrolysis catalysed by acid also increases during use of the material. If the pH is too high, hydrolysis is also increased, i.e. undesired. The dental material comprises modified cellulose nanocrystals (mCNCs), which have been modified to be hydrophobic. The amount of the mCNCs may be for examples 5-30 wt-% of the total weight of the dental material. Indeed, the amount of the mCNCs may be for example from 1, 2, 3, 4, 5, 7, 9, 10, 12, 15, 17, 20, 23, 25, 27, 30 or 35 wt-% up to 2, 3, 4, 5, 7, 9, 10, 12, 15, 17, 20, 23, 25, 27, 30, 35, 40 or even 45 wt-% of the total weight of the dental material.

The CNCs have thus been modified to be hydrophobic. Indeed, inherently, CNCs are predominantly hydrophilic, similar to cellulose. Thus, they may attach to the structure of dentin, but the compatibility with dental material is limited because dental materials are generally methacrylate-based. However, different properties for CNCs can be obtained through surface modification, which are typically performed either covalently or non-covalently on the surface of CNCs and known as such.

Generally, CNCs are obtained from acid hydrolysis. The conditions for the acid hydrolysis are decided in order that the inherent disordered regions of cellulose are hydrolysed and removed, but the crystalline regions stay untouched.

Commonly, a suspension obtained from acid hydrolysis is diluted into water and further centrifuged. These stages are followed by dialysis, whose main purpose is to remove the acid and the reaction products from the dispersion. Additionally, filtration, further centrifugation and ultrasonic treatment are often followed. A common method to remove solvent water from the CNCs is to use freeze-drying.

The composition and concentration of the acid, as well as the ratio between cellulose fibres and the acid largely affect the yield of CNCs. Most widely used acids for the production of CNCs are sulfuric and hydrochloric acids, even though the use of hydrochloric acid has been reported to flocculate the aqueous suspension, and also to limit the CNCs ability to disperse. A suggested concentration for the sulphuric acid in order to obtain CNCs is approximately 65% (wt/wt). There are two optional ways for the process: protonation of glycosidic oxygen or cyclic oxygen. The reaction is followed by decomposition of cellulose and intervention of water. Additionally, the presence of sulphuric acid, which acts as a catalyst, results in esterified hydroxyl groups which yield negatively charged sulphate groups on the surface of CNC.

Pristine CNCs are hydrophilic due to the inherent properties of the cellulose. Therefore, they poorly disperse into non-polar organic solvents or monomers and have a limited adhesion to a hydrophobic matrix of a composite. Chemical functionalisation of CNCs can improve these properties, thus giving CNCs higher dispersibility and compatibility to solvents and matrices, which are used in composites.

Three different kinds of hydroxyl groups on the surface of CNCs provide multiple choices for chemical modification of CNCs. The most frequent modification is reacted to the sixth position hydroxyl, which acts as a primary alcohol. In literature, several modification methods for CNCs have been presented, including inter alia esterification, silylation, polymer grafting and non-covalent surface modifications.

Esterification refers to a reaction between an alcohol and an acid. There are several different methods to manufacture esterified CNCs have been reported. The most common esterification for CNCs is carried out in acid hydrolysis, when a sulphate group is esterified on the surface of the CNC. This esterification reaction is also known as sulphation since sulphate esters are present.

Additionally, another esterification method is acetylation. It can be for example acetylation of vinyl acetate into the surface of CNCs in tetrahydrofuran (THF) dispersion. Yet another esterification method is acylation, for example an alkenyl succinic anhydride (ASA) modification of CNCs. In this surface acylation, two different ASAs; iso-ODSA (iso-octadecenyl succinic anhydride) and n-TDSA (n-tetradecenyl succinic anhydride), are dispersed into water. The resulted modification confers improved hydrophobicity for CNCs. It is typical that esterification is used as a base for polymer grafting. For instance, it is possible to carry out covalent esterification of CNCs with 10-undecenoyl chloride in acetonitrile. The modified CNCs have hydrophobic hydrocarbon brushes on the surface, which provides them with improved compatibility with hydrophobic polymer matrices. Moreover, vinyl group provide CNCs with improved reactivity.

A still further modification method is silylation, in which a silyl group is introduced on the surface of CNC. There are several silane coupling agents which improve the interaction of CNCs to polymer composites. For instance, different pre-hydrolysed alkoxysilanes in ethanol can be adsorbed onto the surface of CNCs. The silane coupling agents, especially MPS, form a covalent bond with CNCs. These silylated CNCs have a high potential to be utilized in polymer matrices. Additionally, a partial silylation of CNCs is known, to obtain an improved attachment in poly(l-lactide) (PLLA) composites.

Yet another modification method is polymer grafting, in which polymer brushes are attached on the surface of CNC. Polymer brushes are thin polymer coatings, which are polymer chains that are attached to the surface from one end. There are two optional methods to do polymer grafting, namely grafting-to approach and grafting-from approach.

In grafting-to approach, pre-synthesised chains of polymers are attached on the surface of CNCs. Commonly, the attachment is obtained either via physisorption or chemisorption, i.e. covalent bonding. Even though grafting-to method is rather straightforward to implement, it has limitations. The outcome is not always preferred, because the method results in decreased grafting density on the surface. Indeed, polymers are forced to diffuse through the already grafted polymers and cannot always reach the free reactive surface.

However, to overcome the low grafting density, grafting-from method can be used. In this method, polymers are grown on the surface of CNCs during the fabrication process using initiator-functionalised surfaces and polymerisation techniques. These techniques allow accurately the control of the functionality, density and thickness of the polymer brushes.

Several polymers have successfully been grafted onto the surfaces of CNCs using grafting-to approach. For instance, poly(ethylene oxide)(PEO)-grafted CNCs have been prepared in aqueous suspensions in order to achieve steric instead of electrostatic stabilisation. Also grafting of thermosensitive amine-terminated statistical polymers, ethylene oxide and propylene oxide copolymers onto the surfaces of CNCs have been carried out by a peptidic coupling reaction.

In addition, it is possible to use grafting-from approach on CNCs, for example to obtain poly(ε-caprolactone) (PCL) modified CNCs by ring-opening polymerisation. It is also known to provide synthesis of CNCs grafted with poly (acrylic acid) (PAA) chains using copper-mediated surface initiated-controlled radical polymerisation.

Furthermore, CNCs can be modified non-covalently. Non-covalent surface modification of CNCs is generally obtained via adsorption of surfactants. A surfactant refers to a material that in low concentration reduces the surface tension of water. It is for example possible to use surfactants consisting of mono- and di-esters of phosphoric acid having alkylphenol tails or to use a cationic surfactant, for example hexadecyl trimethyl ammonium (HDTMA) bromide.

According to an embodiment, the cellulose nanocrystals have been modified with a vinyl group containing organic ester. One suitable modification agent is 10-undecenoyl chloride. The degree of modification is preferably one, i.e. approximately one out of the three hydroxyl-groups on the surface of the cellulose have been modified. Indeed, the maximum degree of modification for cellulose is three, wherein all the three hydroxyl-groups of the cellulose have been modified. It is to be kept in mind that typically modification only occurs on the surface of the cellulose nanocrystals, the inner parts are not modified.

The thermoset methacrylate-based polymer of the dental material may be any suitable polymer. For example, methacrylate-based polymer may be made of monomers selected from the group consisting of methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, acrylic acid, diethylene glycol dimethacrylate, triethylene glycol dimethacrylate (TEGDMA), diurethane dimethacrylate, 2,2-bis (4-(2-hydroxy-3-methacryloxy)phenyl)propane (BisGMA), methacrylate functionalized dendrimers, other methacrylated hyperbranched oligomers and mixtures thereof. The polymer may thus be either a homopolymer or a copolymer and it may comprise more than one metacrylate groups.

According to an embodiment, the thermoset methacrylate-based polymer is a copolymer comprising a hydrogel. In general, hydrogels are composed of a network of hydrophilic polymers, which have a high capacity to retain water. Indeed, a hydrogel is a macromolecular polymer gel constructed of a network of crosslinked polymer chains. Hydrogels are synthesised from hydrophilic monomers by either chain or step growth, along with a functional crosslinking agent to promote network formation. A net-like structure along with void imperfections enhance the hydrogel's ability to absorb large amounts of water via hydrogen bonding. A typical hydrogel has at least one hydroxyl-group that makes it a hydrogel, i.e. highly reactive with water.

According to an embodiment, the hydrogel is 2-hydroxyethyl methacrylate or a mixture of 2-hydroxyethyl metacrylate with another metacrylate.

According to an embodiment, the thermoset methacrylate-based polymer is a copolymer constituted of 70-95 wt-% of 2-hydroxyethyl methacrylate (HEMA) and 5-30 wt-% of triethylene glycol dimethacrylate (TEGDMA). The composition of the monomers making up the polymer may be for example 90:10 HEMA/TEGDMA or 80:20 HEMA/TEGDMA.

According to an embodiment, the dental material is a dental adhesive, a dental composite or a mixture thereof, i.e. a material that is both a composite and adhesive.

The present description also relates to a method for manufacturing a dental material, comprising modifying cellulose nanocrystals to be hydrophobic, mixing the modified cellulose nanocrystals with at least one thermoset methacrylate-based monomer and polymerising the monomers to form a polymer. According to an embodiment, the polymerisation is carried out in a non-aqueous solution. Indeed, the monomers are used in an organic media, which is different from water.

The embodiments listed above in connection with the dental material apply mutatis mutandis to the present method.

Experimental Part

The experimental part covers the preparation of CNCs from filter paper using sulphuric acid hydrolysis. Further, the pristine CNCs were modified with 10-undecenoyl chloride, a long hydrocarbon chain with a vinyl group on the tail, in order to get an improved hydrophobicity on the surface of CNCs. In the following, the percentage is a weight-percentage, unless otherwise indicated.

Materials and Devices Used in the Experiments

Whatman 1 filter paper was used for grinding, Spectra/por 1 dialysis bag was used for dialysis, and Whatman 541 filter paper was used for Büchner funnel filtering. 3 Å molecular sieves were used in the synthesis of the modified CNCs, as well as Spectra/por 1 dialysis bag for dialysis. The device CURE Cordless II (Spring Health Products, Inc., output wavelength 440-460 nm) was used for light curing.

The chemical compounds used were as follows.

Sulphuric acid (96%, Sigma-Aldrich); sodium hydroxide (NaOH, 0.1 M); acetonitrile (99%, Sigma-Aldrich); 10-undecenoyl chloride (97%, Sigma-Aldrich); pyridine (99.9%, Sigma-Aldrich); 4-(dimethylamino)pyridine (DMAP, 99.9%, Sigma-Aldrich); ethanol (Etax Aa, 99.5%); (1R)-(−)-camphorquinone (99%, Sigma-Aldrich); 2-(dimethylamino)-ethyl methacrylate (DMAEMA, 98%, Sigma-Aldrich); 2-hydroxyethyl methacrylate (HEMA, 97%, Sigma22 Aldrich); triethylene glycol dimethacrylate (TEGDMA, 95% Sigma-Aldrich), bisphenol A-glycidyl methacrylate (bis-GMA, Esschem).

Sample Preparation

Preparation of Cellulose Nanocrystals

A Wiley mill was used to grind 15 g of cellulose. The obtained cellulose powder was mixed with 409 g of 64% sulphuric acid ($H_2SO_4$). The mixture was heated to 45° C. and kept in that temperature for 45 minutes under continuous mechanical stirring. After 45 minutes, the reaction was stopped and the acid/cellulose mixture was poured into 3000 ml water in a large beaker. The mixture was left overnight to sediment.

Next day, the sedimented mixture was decanted, and centrifuged for 25 minutes at 6000 rpm. Further, the supernatant was decanted and again centrifuged, however now using a smaller centrifuge with the speed of 2500 rpm for 45 minutes. After the centrifugation, the residues from the tubes were placed in a dialysis bag. The dialysis was continued for three days in a 5 litre beaker with water, and during that time the water surrounding the bag was changed twice per day. When the conductivity of the solution was under 5, ion-exchange was performed by dropwise adding a NaOH solution to the suspension until the pH was over 7. The dialysis was again continued for three days with water until the conductivity was under 5.

After the dialysis, the mixture was filtered in a Büchner funnel. The obtained filtration was a suspension of cellulose nanocrystals. In order to get dry crystals, the suspension was freeze-dried for three days. Finally, CNCs were extracted in ethanol for 48 h in a Soxhlet device in order to remove impurities that were not removed during the water dialysis.

Synthesis of 10-Undecenoyl Modified CNCs

The modification of CNCs by 10-undecenoyl was done as explained below.

Firstly, acetonitrile was dried over 3 Å molecular sieves for two days to prevent any water molecules being present in the reaction. Secondly, 100 ml of dry acetonitrile and 0.520 g of dry CNCs were dispersed using an ultrasonic tip for 60 minutes. After, dispersion was put under magnetic stirring, and simultaneously degassed with nitrogen for two hours. After degassing with nitrogen, the dispersion was cooled to 0° C., and 1040 µl pyridine and a catalytic amount of solid DMAP were carefully added. Also, 1380 µl 10-undecenoyl chloride was added. Magnetic stirring was continued throughout the additions. The reaction was allowed to warm up to room temperature and stirring was continued overnight. Next day, the reaction was cooled again to 0° C., and 1000 μl pyridine and 700 μl 10-undecenoyl chloride were added. The reaction was stirred with a magnet for four days.

The sample was purified by dialysis against water for four days in order to remove chloride and other possible ions. Moreover, the dialysis was continued against ethanol for four days in order to remove organic compounds from the sample. In order to enable freeze-drying, the sample was again dialysed against water, and finally freeze-dried for five days to obtain dry mCNCs.

Application of mCNCs into a Matrix

The dry mCNCs obtained from freeze-drying were applied into a matrix. The matrix consisted either of HEMA/TEGDMA or bis-GMA/TEGDMA. Altogether, eight different samples were prepared. Table 1 illustrates the composition of each sample. The fabrication process is described for 90:10 HEMA/TEGDMA with 20 wt/wt % of mCNCs in the following. A similar working method, and the same amount of (1R)-(−)-camphorquinone (CQ) and 2-(dimethylamino)ethyl methacrylate (DMAEMA), was used for the other samples. However, in some samples, the ratio of HEMA and TEGDMA was 80:20 or 40:60, while in the case of bis-GMA/TEGDMA, the ratio was 50:50 for all samples.

TABLE 1

Composition of the samples

90:10 HEMA/TEGDMA without mCNCs
90:10 HEMA/TEGDMA with 5% of mCNCs
90:10 HEMA/TEGDMA with 10% of mCNCs
90:10 HEMA/TEGDMA with 20% of mCNCs
80:20 HEMA/TEGDMA without mCNCs
80:20 HEMA/TEGDMA with 20% of mCNCs
40:60 HEMA/TEGDMA without mCNCs
40:60 HEMA/TEGDMA 9% mCNCs
40:60 HEMA/TEGDMA 10% mCNCs
50:50 bis-GMA/TEGDMA without mCNCs
50:50 bis-GMA/TEGDMA with 10% of mCNCs First, 7.5 mg (0.7 wt/wt %) of (1R)-(−)-camphorquinone, used as a photo-initiator, and 0.2146 g (20 wt/wt %) of mCNCs were weighted into a glass bottle, as typically used in chromatography. Then, 900 μl of HEMA and 98 μl of TEGDMA were added to prepare a mixture with the ratio of 90:10 HEMA/TEGDMA. TEGDMA was used in HEMA matrix in order to improve the stabilisation and the polymerisation of HEMA. Ultrasonic bath was used for 10 minutes to mix the ingredients. After ultrasonication, 8 μl (0.7 wt/wt %) of 2-(dimethylamino)ethyl methacrylate (DMAEMA), used as a co-initiator, was added. The addition of DMAEMA improved the hardening of HEMA hydrogel. Further, stirring the mixture was performed with a Vortex mixer.

After the preparation of the mixture, test specimens for dynamic mechanical analysis were prepared. Some of the adhesive mixture was poured on a Teflon® plate, inside a metallic washer with an inside diameter of 11 mm and height of 2 mm. Light curing was used for 40 seconds to harden the adhesive. Finally, polymerized HEMA hydrogel was detached from the metallic washer.

Further, test specimens for three-point bending strength test were also prepared. Metallic moulds with dimensions of 2 mm×2 mm×25 mm were used, while the mould was filled with the material in one layer. The upper surface was evened with a piece of Mylar-foil and microscope glass plate was set on top of the mould and pressed down to get even surface.

The specimen was then hand light cured for 3×20 s from each side of the mould and the specimens were grinned with 2000 grit SiC-paper and set in to an incubator+37° C. for 72 h prior to testing. Five parallel samples were prepared from the material according to the present description and from the reference material (without modified CNC).

Test Methods

Dynamic Mechanical Analysis

Young's modulus, also known as elastic modulus, refers to the stiffness of a solid material. It can be determined as the ratio of stress to strain. Whereas stress refers to the force applied to the area, strain represents the deformation of the material after stress. In this experiment, it was tested how the amount of CNCs on one hand, and the amount of TEGDMA with respect to HEMA on the other hand impacts on the stiffness of the material. The mechanical test was performed in dynamic mechanical analysis (DMA). Dynamic mechanical analyser Q800 (TA instruments) with compression mode was used. Compressive strength of the composites was measured in compression test, in which 1 N to 18 N force was applied in time interval of 18 minutes in room temperature.

Three-Point Bending Test

The three-point bending test is another way to test mechanical properties of a material. The test was performed with Lloyd LR30kPlus mechanical testing device, with a 2500 N sensor and using standard ISO 4049, 2009(E) (Dentistry-Polymer based filing, restorative and luting materials). Parameters used in the test were as follows.

Direction: Compression
Preload: 1 N
Preload speed: 10 mm/min
Extension rate: 1 mm/min
Stop test: extension 10 mm, stop test when load drops 30%
Test method: 3-point bending
Span length: 20 mm The Determination of the Degree of Conversion The degree of conversion of monomer to polymer was measured in FTIR (Fourier transform infrared spectroscopy) with an ATR (attenuated total reflectance) attachment (Perkin Elmer, FT-IR Spectrometer Frontier). The sample was poured on the ATR diamond, inside a metallic washer with a diameter of 5.4 mm and height of 1.2 mm. IR spectrum was measured after the placement, and next light cured for 40 seconds with Elipar S10 LED curing light (3M, range of wavelength for polymerization 430-480 nm) for the HEMA/TEGDMA samples and for 20 s for the bis-GMA/TEGDMA samples. Directly after light curing, IR spectrum was measured every two minutes during ten minutes. For the results, the degree of conversion was calculated using equation (1)

$$\text{Degree of conversion, \%} = \frac{C_{aliphatic}/C_{carbonyl}}{U_{aliphatic}/U_{carbonyl}} \quad (1)$$

where C is aliphatic and carbonyl peaks ratio from light cured sample, and U is aliphatic and carbonyl peaks ratio from uncured sample.

Results and Discussion

10-Undecenoyl Modified CNCs

To improve the compatibility with HEMA matrix, CNCs were modified with 10-undecenoyl chloride in acetonitrile. The successful 10-undecenoyl modification of CNCs was observed as a yellow colour of the reaction after the additions and four days of magnetic stirring. The completeness of modification and purification of the dialysis was confirmed with FTIR. FTIR spectra for pristine CNCs and mCNCs are shown in FIG. 1, where the wavenumber in cm$^{-1}$ is given on the abscissa and the transmittance in percentage is given on the ordinate.

The use of water and ethanol in dialysis resulted in relatively pure mCNCs. In FTIR spectrum, the completeness of modification process can be verified with the presence of a strong ester carbonyl stretching band at 1752 cm$^{-1}$. This peak can be observed in the lower part of FIG. 1, but not in the upper part of FIG. 1. Moreover, the peaks at 915 cm$^{-1}$, 1644 cm$^{-1}$ and 3082 cm$^{-1}$ refer to the primary alkene of the hydrocarbon chain. The presence of saturated hydrocarbon chain is confirmed with the peaks at 2860 cm$^{-1}$ and 2930 cm$^{-1}$.

In the synthesis of 10-undecenoyl modified CNCs, the purification of mCNCs was completed in dialysis against water and ethanol. Ethanol dialysis was used for the removal of carboxylic acid.

Modified CNCs in HEMA Matrix

Dispersibility of pristine CNCs in comparison to modified CNCs in HEMA matrix was studied comparing the mixtures with the naked eye after ultrasonication. The results show that modification significantly improved the compatibility of mCNCs with 80:20 HEMA/TEGDMA matrix.

Moreover, the sedimentation of mCNCs was examined. Due to the yellow colour of the mixture, obtained from (1R)-(−)-camphorquinone, the slight sedimentation of mCNCs could not be documented after one day. However, without (1R)-(−)-camphorquinone, the slight sedimentation of mCNCs could be seen. Also, total sedimentation of mCNCs was reached in three days. Thus, dispersion of HEMA and mCNCs was not long-term stable, but due to the viscosity of the mixture, sedimentation was slow.

The modification of CNCs significantly improved the compatibility with HEMA matrix. Pristine CNCs did not disperse into HEMA, while mCNCs seemed to be well-dispersed in HEMA matrix. Supported by this, as well as the FTIR spectra, the modification of CNCs was considered to be successful.

Dynamic Mechanical Analysis

The compressive strength of the samples was measured with dynamic mechanical analysis. The measurements were carried out for samples with 10 min ultrasonication. In addition, to obtain a reference sample, dynamic mechanical analysis was performed for 50:50 BisGMA/TEGDMA resin (including 0.7 wt/wt % of (1R)-(−)-camphorquinone and DMAEMA, BisGMA standing for 2,2-bis-[4-[methacryloxypropoxy)-phenyl]-propane). Table 2 presents the ratio of stress to strain, also referred as Young's modulus, for each sample. The values of Young's modulus were determined from the graphs obtained in dynamic mechanical analysis. The slope was calculated in the beginning of the curve, since the properties of the samples can be affected by the increased in force during the dynamic mechanical analysis measurement.

TABLE 2

| Sample | Young's modulus (MPa) |
|---|---|
| 90:10 HEMA/TEGDMA without mCNCs | 0.14 ± 0.01% |
| 90:10 HEMA/TEGDMA 5% mCNCs | 0.17 ± 0.02% |
| 90:10 HEMA/TEGDMA 10% mCNCs | 0.46 ± 0.25% |
| 90:10 HEMA/TEGDMA 20% mCNCs | 0.64 ± 0.21% |
| 80:20 HEMA/TEGDMA without mCNCs | 0.15 ± 0.02% |
| 80:20 HEMA/TEGDMA 20% mCNCs | 0.68 ± 0.26% |
| 50:50 BisGMA/TEGDMA without mCNC | 0.66 ± 0.22% |

Figure 2:
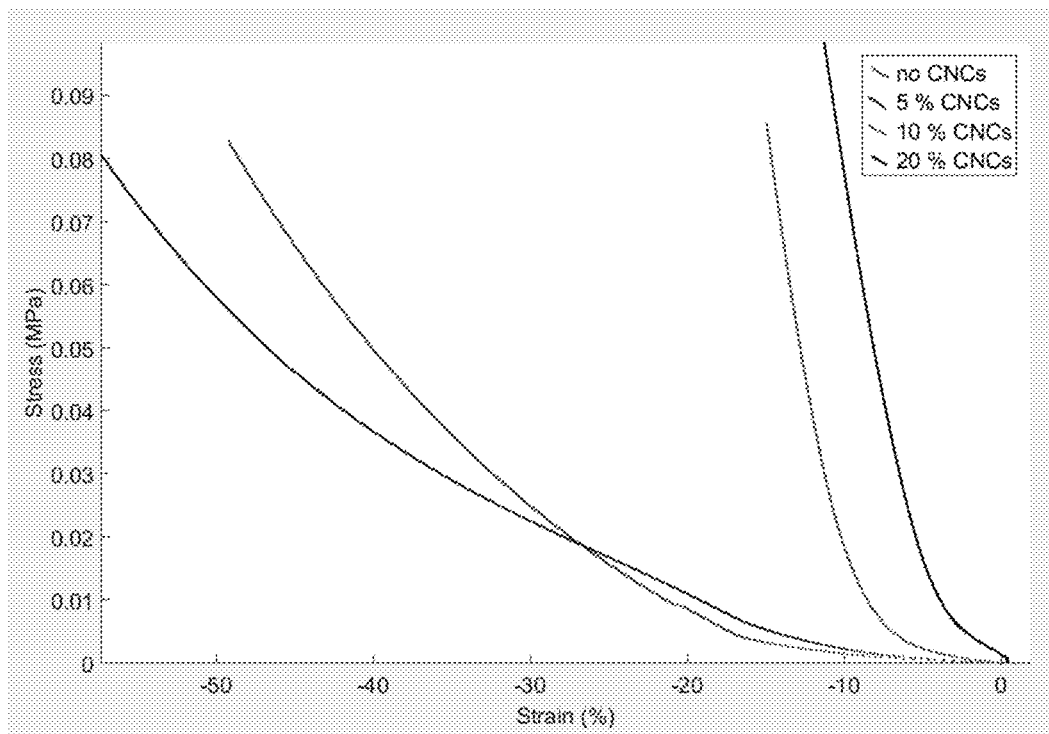
FIG. 2 illustrates the impact of the amount of mCNCs on the value of Young's modulus.

According to Table 2, the value of Young's modulus positively correlates with the increase in the amount of mCNCs in the composite. The observation is illustrated in FIG. 2, wherein the strain in percentage is given on the abscissa and the stress in MPa is given on the ordinate for the samples with 90:10 HEMA/TEGDMA. In FIG. 2, when seen in the upper part of FIG. 2, the first curve from the left illustrates the results for the sample with 5% mCNCs, the second curve from the left illustrates the results for the sample without mCNCs, the third curve from the left illustrates the results for the sample with 10% mCNCs, and the curve on the right illustrates the results for the sample with 20% mCNCs.

Figure 3:
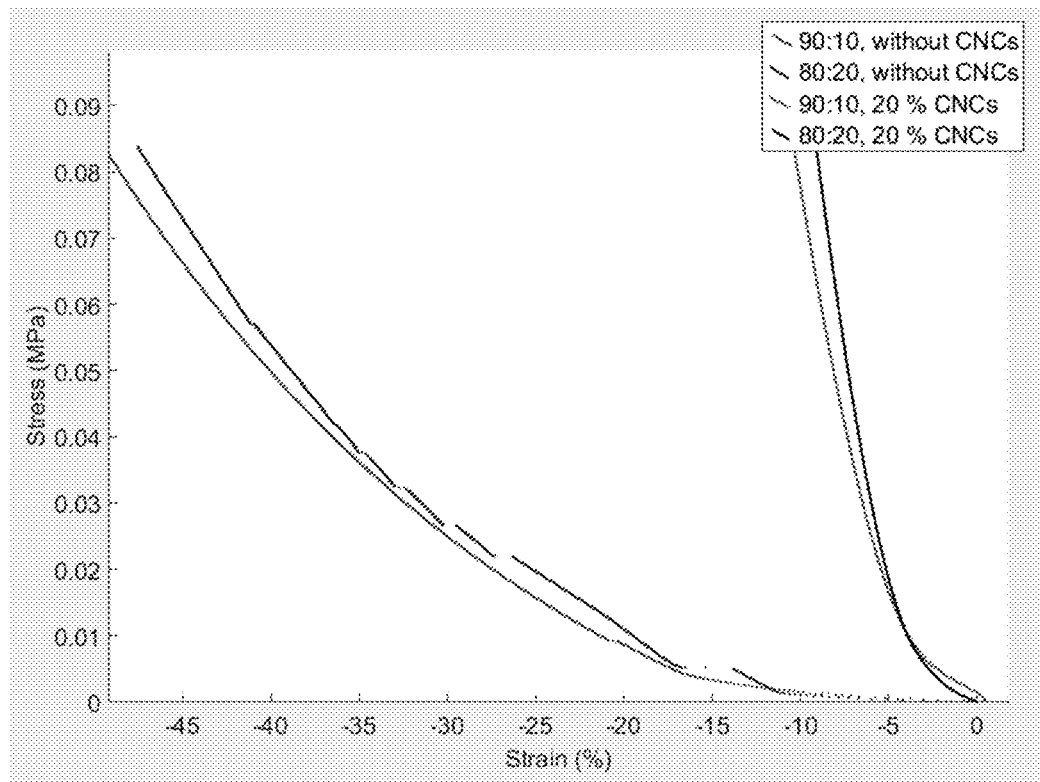
FIG. 3 illustrates the impact of TEGDMA on the value of Young's modulus.

Moreover, increase in TEGDMA in relation to HEMA is also observed to slightly increase the value of Young's modulus, even though the values are overlapping inside the error limits. The impact of TEGDMA on the value of Young's modulus is illustrated in FIG. 3, wherein the strain in percentage is given on the abscissa and the stress in MPa is given on the ordinate. In FIG. 3, when seen in the upper part of FIG. 3, the first curve from the left illustrates the results for the sample of 90:10 HEMA/TEGDMA without mCNCs, the second curve from the left illustrates the results for the sample of 80:20 HEMA/TEGDMA without mCNCs, the third curve from the left illustrates the results for the sample of 90:10 HEMA/TEGDMA with 20% mCNCs, and the curve on the right illustrates the results for the sample of 80:20 HEMA/TEGDMA with 20% mCNCs.

Figure 4:
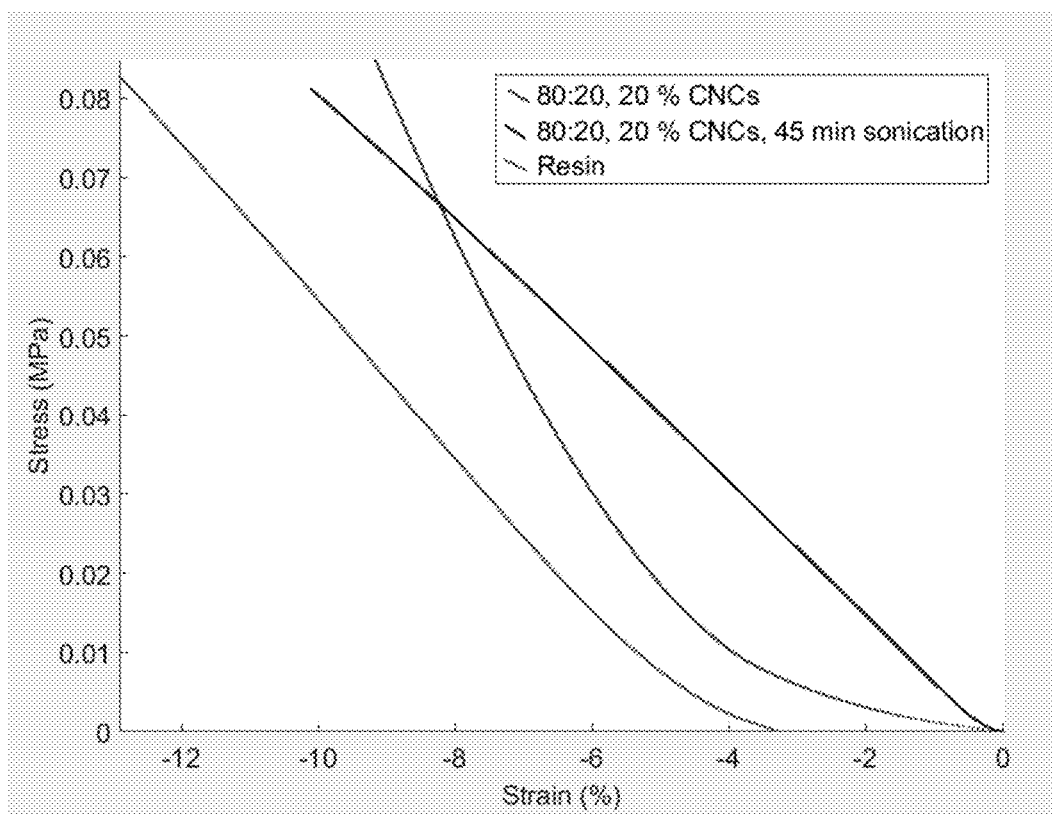
FIG. 4 illustrates the impact of ultrasonication on the value of Young's modulus.

Finally, the impact of prolonged ultrasonication on the value of Young's modulus was studied, and the results were compared to the value of Young's modulus for the reference resin (FIG. 4, wherein the strain in percentage is given on the abscissa and the stress in MPa is given on the ordinate). In FIG. 4, the impact of ultrasonication is illustrated and when seen in the uppermost part of FIG. 4, the first curve from the left illustrates the results for the sample of 80:20 HEMA/TEGDMA without mCNCs, the middle curve illustrates the results for the sample of 80:20 HEMA/TEGDMA with 20% of mCNCs and 45 minutes of ultasonication mCNCs, and the curve on the right illustrates the results for the sample of 80:20 HEMA/TEGDMA with 20% mCNCs with 10 minutes of ultrasonication.

As seen in Table 2, the values with 10 min and 45 min ultrasonication are nearly the same, and thus prolonged ultrasonication is observed not to have an impact on the Young's modulus of the composite. Indeed, as the value of Young's modulus for the resin equals to the value of Young's modulus for 80:20 HEMA/TEGDMA with 20% of mCNCs, the materials can be said to be similar in stiffness.

The results of dynamic mechanical analysis reveal that stiffness of the material increases when the amount of mCNCs is increased, and slightly if any when TEGDMA is increased. As presented in Table 2, the highest Young's modulus value is obtained for the sample 80:20 HEMA/TEGDMA with 20% of mCNCs.

Three-Point Bending Test

The samples with 50:50 bis-GMA/TEGDMA without mCNC and with 10% mCNC were tested with the above-mentioned three-point bending test. The results are given in Table 3.

TABLE 3

| | Young's Modulus of bending (MPa) | Load at maximum load (N) | Maximum bending stress at maximum load (MPa) | Work from preload to break (Ncm) |
|---|---|---|---|---|
| 50:50 bis-GMA/TEGDMA without mCNC | 1843.66 | 25.88 | 94.88 | 4.25 |
| 50:50 bis-GMA/TEGDMA 10% mCNC | 1628.83 | 17.58 | 66.23 | 1.54 |

The results show that the results are not significantly lower for the samples with modified CNCs than for samples without any particles.

The Degree of Conversion

The conversion of monomer to polymer was measured in FTIR with an ATR attachment (Perkin Elmer, FT-IR Spectrometer Frontier). The aim of the measurement was to verify the results obtained in dynamic mechanical analysis.

Table 4 represents the degree of conversion for each sample. Perfectly polymerised material has a degree of conversion of 100%.

TABLE 4

| Sample | Degree of conversion |
|---|---|
| 90:10 HEMA/TEGDMA without mCNCs | 13.2 ± 0.49% |
| 90:10 HEMA/TEGDMA 10% mCNCs | 17.4 ± 1.15% |
| 90:10 HEMA/TEGDMA 20% mCNCs | 27.0 ± 5.94% |
| 80:20 HEMA/TEGDMA without mCNCs | 16.1 ± 0.73% |
| 80:20 HEMA/TEGDMA 20% mCNCs | 33.5 ± 1.71% |
| 40:60 HEMA/TEGDMA without mCNCs | 31.7 |
| 40:60 HEMA/TEGDMA 9% mCNCs | 36.3 ± 7.30% |
| 40:60 HEMA/TEGDMA 10% mCNCs | 34.4 ± 9.70% |
| 50:50 bis-GMA/TEGDMA without mCNCs | 59.9 |
| 50:50 bis-GMA/TEGDMA 10% mCNCs | 58.8 ± 1.4% |

The results show that the conversion of monomer to polymer increases when the amount of mCNCs and TEGDMA is increased. In parallel samples (same resin, with or without mCNCs), the addition of mCNCs has either no effect or it improves the degree of conversion. However, for samples with 20% of mCNCs, the value of the degree of conversion overlaps due to the wide limit of error for sample 90:10 HEMA/TEGDMA with 20% of mCNCs. The inaccuracy is supposed to occur due to the observed aggregation in the sample before ATR measurement. Thus, the measured quantities were supposedly not equal in the content. However, the results of ATR measurements strongly support the results of dynamic mechanical analysis: greater amount of mCNCs and TEGDMA improves the stiffness of the material. Hence, addition of TEGDMA improves the stabilization and the polymerisation of HEMA matrix.

The invention claimed is:

1. A dental material comprising a thermoset methacrylate-based polymer resin and cellulose nanocrystals, wherein the cellulose nanocrystals have been modified to be hydrophobic, and wherein the cellulose nanocrystals have been modified with a vinyl group containing organic ester.

2. A dental material according to claim 1, comprising 5-30 wt-% of the cellulose nanocrystals.

3. A dental material according to claim 1, wherein the cellulose nanocrystals have been modified with 10-undecenoyl chloride.

4. A dental material according to claim 1, wherein the methacrylate-based polymer resin is selected from a group consisting of homopolymers and copolymers of methyl methacrylate, ethyl methacrylate, n-butyl methacrylate, isobutyl methacrylate, 2-ethylhexyl methacrylate, 2-hydroxyethyl methacrylate, cyclohexyl methacrylate, isobornyl methacrylate, tetrahydrofurfuryl methacrylate, benzyl methacrylate, morpholinoethyl methacrylate, acrylic acid, diethylene glycol dimethacrylate, triethylene glycol dimethacrylate, diurethane dimethacrylate or 2,2-bis(4-(2-hydroxy-3-methacryloxy)phenyl) propane (BisGMA).

5. A dental material according to claim 1, wherein the methacrylate-based polymer is a copolymer comprising a hydrogel.

6. A dental material according to claim 5, wherein the hydrogel comprises 2-hydroxyethyl methacrylate.

7. A dental material according to claim 1, further comprising filler particles.

8. A dental material according to claim 1, wherein the methacrylate-based polymer is a copolymer constituted of 70-95 wt-% of 2-hydroxyethyl methacrylate and 5-30 wt-% of triethylene glycol dimethacrylate.

9. A dental material according to claim 1, wherein the dental material is a dental adhesive and/or a dental composite.

10. A method for manufacturing a dental material, comprising
modifying cellulose nanocrystals to be hydrophobic, wherein the cellulose nanocrystals have been modified with a vinyl group containing organic ester;
mixing the modified cellulose nanocrystals with at least one thermoset methacrylate-based monomer; and
polymerising the monomers to form a polymer.

11. A method according to claim 10, wherein the polymerisation is carried out in a non aqueous solution.

* * * * *